US010258947B2

(12) United States Patent
Ozeki

(10) Patent No.: US 10,258,947 B2
(45) Date of Patent: Apr. 16, 2019

(54) MIXING DEVICE

(71) Applicant: ULVAC, INC., Chigasaki-shi, Kanagawa (JP)

(72) Inventor: Tomomitsu Ozeki, Chigasaki (JP)

(73) Assignee: ULVAC, INC., Chigasaki-shi, Kanagawa (JP)

(*) Notice: Subject to any disclaimer, the term of this patent is extended or adjusted under 35 U.S.C. 154(b) by 4 days.

(21) Appl. No.: 15/809,195

(22) Filed: Nov. 10, 2017

(65) Prior Publication Data

US 2018/0154321 A1 Jun. 7, 2018

(30) Foreign Application Priority Data

Nov. 11, 2016 (JP) .................................. 2016-220266

(51) Int. Cl.
| | | |
|---|---|---|
| B01F 13/08 | (2006.01) | |
| B01F 13/10 | (2006.01) | |
| B01F 7/00 | (2006.01) | |
| B01F 7/16 | (2006.01) | |
| B01F 15/00 | (2006.01) | |
| C12M 1/32 | (2006.01) | |
| C12M 1/06 | (2006.01) | |

(52) U.S. Cl.
CPC ...... *B01F 13/1022* (2013.01); *B01F 7/00841* (2013.01); *B01F 7/1665* (2013.01); *B01F 13/0845* (2013.01); *B01F 15/00389* (2013.01); *C12M 23/12* (2013.01); *C12M 27/02* (2013.01); *B01F 2215/0037* (2013.01)

(58) Field of Classification Search
CPC ............. B01F 13/0827; B01F 13/0845; B01F 13/1022

USPC .................................................. 366/273, 274
See application file for complete search history.

(56) References Cited

U.S. PATENT DOCUMENTS

| | | | | |
|---|---|---|---|---|
| 6,306,658 | B1* | 10/2001 | Turner | B01F 15/00207 436/37 |
| 6,357,907 | B1* | 3/2002 | Cleveland | B01F 13/0818 366/273 |
| 6,467,946 | B1* | 10/2002 | Gebrian | B01F 7/005 366/273 |
| 7,288,229 | B2* | 10/2007 | Turner | B01F 15/00454 422/130 |
| 9,616,398 | B2* | 4/2017 | Chien | B01F 7/005 |

(Continued)

FOREIGN PATENT DOCUMENTS

| | | |
|---|---|---|
| JP | 2007-074900 A | 3/2007 |
| WO | WO-2016/116972 A1 | 7/2016 |

*Primary Examiner* — David L Sorkin
(74) *Attorney, Agent, or Firm* — Saliwanchik, Lloyd & Eisenschenk

(57) ABSTRACT

Provided is a mixing device that is configured to install therein a multi-well plate including a plurality of wells capable of containing matter to be mixed and includes mixing mechanisms each of which mixes the matter to be mixed with a motor and is provided for each of the wells. The mixing mechanisms each includes a first rotator that is connected to the motor and rotates due to activation of the motor, a mixing rod that mixes the matter to be mixed, a second rotator that supports the mixing rod, a magnetic coupling mechanism that magnetically couples the first rotator to the second rotator, and a seal ring that surrounds an opening of the well and is capable of closing the well together with the second rotator.

15 Claims, 12 Drawing Sheets

(56) References Cited

U.S. PATENT DOCUMENTS

| | | | |
|---|---|---|---|
| 2003/0031089 A1* | 2/2003 | Schwarz | B01F 13/0818 366/273 |
| 2008/0205190 A1* | 8/2008 | Cleveland | B01F 13/0818 366/273 |
| 2013/0126436 A1* | 5/2013 | Ok | B03C 1/30 210/695 |

* cited by examiner

MIXING DEVICE

CROSS REFERENCE TO RELATED APPLICATIONS

This application claims the benefit under 35 U.S.C 119 of Japanese Patent Application No. 2016-220266, filed Nov. 11, 2016, the disclosure of which is herein incorporated by reference in its entirety.

BACKGROUND

The present invention relates to a mixing device for mixing solution in a well plate.

Multi-well plates, which are also called microplates, micro-well plates, microtiter plates, or the like, are widely used as an experimental or testing instrument in the field of study in medical science, pharmaceutics, biochemistry, chemistry, and the like. The multi-well plate generally has, for example, 6, 24, 96, 384, or 1536 wells. Each of the wells is capable of containing approximately 1 microliter to several milliliters of reaction solution. A plate reader is used for detecting the solution after reaction. Moreover, an automatic solution addition and suction device for adding solution and washing wells, a conveyance system for conveying a plate itself, and the like are commercially available as general-purpose products from various manufacturers.

A cell-based assay for evaluation of function on a cell-by-cell basis has recently attracted attention. Multi-well plates are often used therefor. For a measurement format used in the cell-based assay, a 96-well plate is predominant, and a 16-well plate and a 384-well plate are also used. Mixing control is important in cell culture and measurement. In the mixing control, it is necessary to mix solution without damaging cells sticking to the bottom or floating cells. Thus, highly accurate mixing is necessary. Since a small amount of reaction solution is contained in a well, if the reaction solution evaporates, it may be difficult to sufficiently mix the reaction solution. In addition, cells contained therein may be damaged. In particular, if volatile reaction solution is used, it is very important to inhibit evaporation of the reaction solution.

It is said that 70% of medicine has a plurality of crystal forms. The solubility and stability are different in each of the crystal forms. Therefore, it is necessary to evaluate as many crystal forms as possible in development processes. In screening such crystal polymorphism, a technology of high-throughput screening in which detailed conditions such as the solution composition, the temperature, and the mixing speed of compound solution are set and crystal forms generated under each of the conditions are evaluated is useful. Also in this case, the multi-well plate is often used. Regarding mixing, horizontal vortex mixing or mixing with a magnetic stirrer is used. In the method using the magnetic stirrer, a setting range of mixing revolutions per minute (rpm) is narrow, and it is not easy to achieve low-speed and high-speed mixing. Further, due to low reliability of motion of the stirrer, if the rotation followability is low, it lowers the mixing efficiency. Further, there is also a problem that the mixing device itself is large in size. Most problematic is that a magnet stirrer disposed on a bottom surface grinds generated crystals during mixing and accurate evaluation results cannot be obtained. Further, in any methods, only one mixing condition can be set in all the wells. Thus, it is desirable to be capable of setting the mixing rpm corresponding to each of the wells in order to consider many detailed mixing conditions. In crystal screening, paddle mixing is often used for scale-up, and hence it is favorable to use paddle mixing also in small-scale experiments.

For synthesis of medicines, high-throughput synthesis techniques represented by combinatorial chemistry is desirable. Synthesis approaches using a microplate have been carried out many times in the past. Typically, horizontal vortex mixing or mixing using a magnetic stirrer is employed. For synthesis of medicines, paddle mixing is often used for scale-up, and hence it is favorable to use paddle mixing also in small-scale experiments.

WO 2016/116972 (hereinafter, referred to as Patent Literature 1) describes a mixing device that mixes solution in a well by using paddle mixing for each of wells of a multi-well plate. In Patent Literature 1, a mixing rod is connected to a motor shaft of a motor and the mixing rod rotates due to activation of the motor for mixing. In the mixing device described in Patent Literature 1, a seal is provided between the mixing rod and a bearing fixed on a motor chassis. Thus, a space communicating with liquid to be mixed is isolated from the bearing fixed on the motor chassis and the liquid to be mixed is inhibited from splashing onto the bearing.

Further, Japanese Patent Application Laid-open No. 2007-74900 (hereinafter, referred to as Patent Literature 2) describes a mixing device using a magnetic coupling mechanism. In Patent Literature 2, in order to mix matter to be mixed in a hermetically sealed container, a driving rotator capable of being rotationally driven by an electric motor is magnetically coupled with a driven rotator on which a mixing blade is mounted, and matter to be mixed is mixed due to activation of the electric motor. In Patent Literature 2, matter that can be mixed only under a hermetically sealed state or matter to be mixed under a high-temperature and high-pressure environment or under vacuum is sealed in the hermetically sealed container. The hermetically sealed container is hollow as a whole and has no openings. The mixing blade, part of a driven shaft on which the mixing blade is mounted, and part of a magnetic rotation transmitter are housed in a hermetically sealed state in the hermetically sealed container. The hermetically sealed container is composed of at least two parts and hermetically sealed with a bolt and a seal member or the like. After mixing, the hermetically sealed container is disassembled within a hermetically sealed box, and the mixed matter is taken out.

SUMMARY

In the mixing device of Patent Literature 2, only one hermetically sealed container in which the matter to be mixed is contained is used. Further, the hermetically sealed container in which the matter to be mixed is contained is composed of two parts and has a configuration hermetically sealed with a bolt and a seal member or the like. Therefore, it is difficult to realize a hermetically sealed structure with a bolt and a seal member or the like as shown in Patent Literature 2 for each of wells of the multi-well plate including a plurality of wells that contains the matter to be mixed.

In view of the above-mentioned circumstances, the present invention has been made to provide a mixing device optimal for a multi-well plate, that is, to provide a mixing device having a configuration for suppressing evaporation of matters to be mixed in wells.

In accordance with an embodiment of the present invention, there is provided a mixing device that is configured to install therein a multi-well plate including a plurality of wells capable of containing matter to be mixed and includes mixing mechanisms each of which mixes the matter to be mixed with a motor and is provided for each of the wells.

The mixing mechanisms each includes a first rotator, a mixing rod, a second rotator, a magnetic coupling mechanism, and a seal ring.

The first rotator is connected to the motor and rotates due to activation of the motor.

The mixing rod mixes the matter to be mixed.

The second rotator supports the mixing rod.

The magnetic coupling mechanism magnetically couples the first rotator to the second rotator.

The seal ring surrounds an opening of the well and is capable of closing the well together with the second rotator.

In the mixing device, a space inside the well in which the mixing rod is housed and a space in which the motor serving as a driving source that rotates the mixing rod is housed are isolated from each other by the magnetic coupling mechanism. Therefore, solution in the well does not evaporate and reach the motor. Further, the seal ring and the second rotator can close the inside of the well. Further, the air tightness in the well is enhanced, evaporation of the solution in the well is reduced.

The second rotator may include a rotational portion that is coupled to the mixing rod, and a bearing provided between the rotational portion and the seal ring.

The rotational portion may include a rotational shaft that is coupled to the mixing rod, the bearing may include an inner race including a through-hole into which the mixing rod and the rotational shaft are inserted, an outer race, and a ball provided between the inner race and the outer race, and the seal ring may have an inner diameter equal to or smaller than an outer diameter of the inner race as the seal ring and the inner race are projected onto a plane orthogonal to the rotational shaft.

With such a configuration, even if the inner race is abraded by the ball of the bearing in long-term use and abrasion debris is produced due to this abrasion, the abrasion debris can be received by the seal ring and inhibited from entering the well because the inner diameter of the seal ring is set to be equal to or smaller than the outer diameter of the inner race.

The bearing may be formed of at least one of a polyetheretherketone (PEEK) resin, a fluorocarbon polymer, and a polyphenylene sulfide (PPS).

With such a configuration, even if solution that is an organic solvent or the like contained in the matter to be mixed splashes onto the bearing or evaporates and is deposited on the bearing, deterioration of the bearing due to the solution that is the organic solvent or the like can be suppressed because a PEEK resin or a fluorocarbon polymer, which is excellent in resistance to solvent, is used for the bearing.

The second rotator may include a rotational portion that is coupled to the mixing rod, and the mixing device may further include a ring member provided between the rotational portion and the seal ring.

The mixing device may further include a casing including a main surface portion that is opposed to an upper surface of the multi-well plate, in which the mixing mechanism is provided in the main surface portion.

The casing may have a stacked structure of a motor-housing casing and a housing.

The motor-housing casing houses the motor and the first rotator for each of the wells.

The housing retains the mixing rod, the second rotator, and the seal ring for each of the wells.

The housing may include a first flat surface that is adjacent to the motor-housing casing, and a second flat surface that is opposed to the first flat surface, and the second flat surface may include housing compartments each being a non-through-hole, being provided for each of the wells, and housing the second rotator.

With such a configuration, the housing is interposed between the second rotator and the motor-housing casing and also interposed between the individual second rotators. With this, the motor-housing casing can hold the housing at the surface thereof. Therefore, pressure can be in-plane uniformly applied on the seal rings each provided for each of the openings of the plurality of wells of the multi-well plate during mixing.

For example, there is a case where the housing is not interposed between the second rotators and the motor-housing casing, a casing in which the plurality of first rotators are arranged and retained in a matrix form and a casing in which the plurality of second rotators are arranged and retained in a matrix form are held at four corners of an outer periphery of each casing, and the first rotators are magnetically coupled with the second rotators. In this case, it is difficult to in-plane uniformly apply pressure on the seal rings each provided for each well. Thus, pressure applied on the seal ring positioned at the center portion of the multi-well plate is lower than pressure applied on the seal rings at other positions. Therefore, along with an increase in the number of wells, the air tightness of a well of the plurality of wells, which is positioned at the center portion of the multi-well plate, is deteriorated in comparison with the wells positioned at the outer periphery of the multi-well plate.

In contrast, the housing is interposed between the second rotators and the motor-housing casing, and hence the pressure can be in-plane uniformly applied on the plurality of seal rings during activation of the mixing device and the air tightness in the plurality of wells can be in-plane uniformly enhanced.

The mixing device may further include a mounting table on which the multi-well plate is placed.

With such a configuration, mixing can be performed while the mounting table and the casing sandwich the multi-well plate at surfaces thereof. With this, the pressure applied on the individual seal rings can be made uniform and the air tightness in the plurality of wells can be in-plane uniformly enhanced.

In the second flat surface of the housing forming a part of the casing, i.e., a surface positioned on a side of the multi-well plate, the housing compartments that are the non-through-holes each provided in each well and houses the second rotator are formed. Therefore, the housing is interposed between the individual second rotators and also interposed between the second rotators and the motor-housing casing. Thus, the multi-well plate can be held by the mounting table and the casing with in-plane uniform pressure. Thus, the air tightness in the plurality of wells can be in-plane uniformly enhanced.

The housing may be formed of at least one of a PEEK resin, a fluorocarbon polymer, and a polyphenylene sulfide (PPS).

With such a configuration, even if an organic solvent or the like contained in the matter to be mixed adheres to the housing, deterioration of the housing due to the organic solvent or the like can be suppressed because a PEEK resin, a fluorocarbon polymer, or a polyphenylene sulfide, which is excellent in resistance to solvent, is used for the housing.

The magnetic coupling mechanism may include a first magnet provided in the first rotator, and a second magnet provided in the second rotator. In this manner, the first rotator and the second rotator can be magnetically coupled with each other by magnetic coupling between the first magnet and the second magnet.

The first rotator may include a first surface and a second surface that are disposed to be opposed to each other in a rotational-axis direction of the first rotator, the first magnet may include two different magnetic poles and is provided in parallel to the rotational-axis direction such that one of the magnetic poles is located on a side of the first surface and the other is located on a side of the second surface, and the magnetic poles of the first magnets, which are located on the side of the first surface, may be all the same in the mixing mechanisms each provided for each of the wells.

With such a configuration, non-uniformity of rotation in the mixing mechanisms is reduced. When the mixing mechanisms using the magnetic coupling mechanisms are simultaneously operated, the mixing mechanisms adjacent to each other interfere with each other and the rotation phases are deviated, which may cause non-uniformity of rotation. It was found that the non-uniformity of rotation is reduced when the magnets that constitute the magnetic coupling mechanisms each corresponding to each well are arranged such that the magnetic poles located on the side of the first surface of the first rotator are all the same.

The motor may be provided for each of the wells.

In this manner, the motor may be provided for each of the mixing mechanisms and driving of the plurality of motors may be individually controlled. With this, each of the mixing rods can be independently rotated. The respective mixing rods may be driven under the same rotation condition or may be driven under different rotation conditions.

The seal ring may be formed of a fluorocarbon polymer or a fluorocarbon rubber.

With such a configuration, even if an organic solvent or the like contained in the matter to be mixed adheres to the seal ring, deterioration of the seal ring due to the organic solvent or the like can be suppressed because a fluorocarbon polymer or a fluorocarbon rubber, which is excellent in resistance to solvent, is used for the seal ring. Further, it is desirable to use an elastic material such as a fluorocarbon polymer and a fluorocarbon rubber for the seal ring. In this case, the air tightness in the well can be enhanced.

Further, the mixing rod may be formed of at least one of a PEEK resin, a fluorocarbon polymer, and a polyphenylene sulfide (PPS).

With such a configuration, deterioration of the mixing rod due to an organic solvent or the like contained in the matter to be mixed can be suppressed because at least one of a PEEK resin, a fluorocarbon polymer, and a polyphenylene sulfide, which is excellent in resistance to solvent, is used for the mixing rod.

As described above, in accordance with the present invention, it is possible to mix solution in the multi-well plate while suppressing evaporation of the solution.

DETAILED DESCRIPTION OF EMBODIMENTS

Hereinafter, embodiments of the present invention will be described with reference to the drawings.

Figure 1:
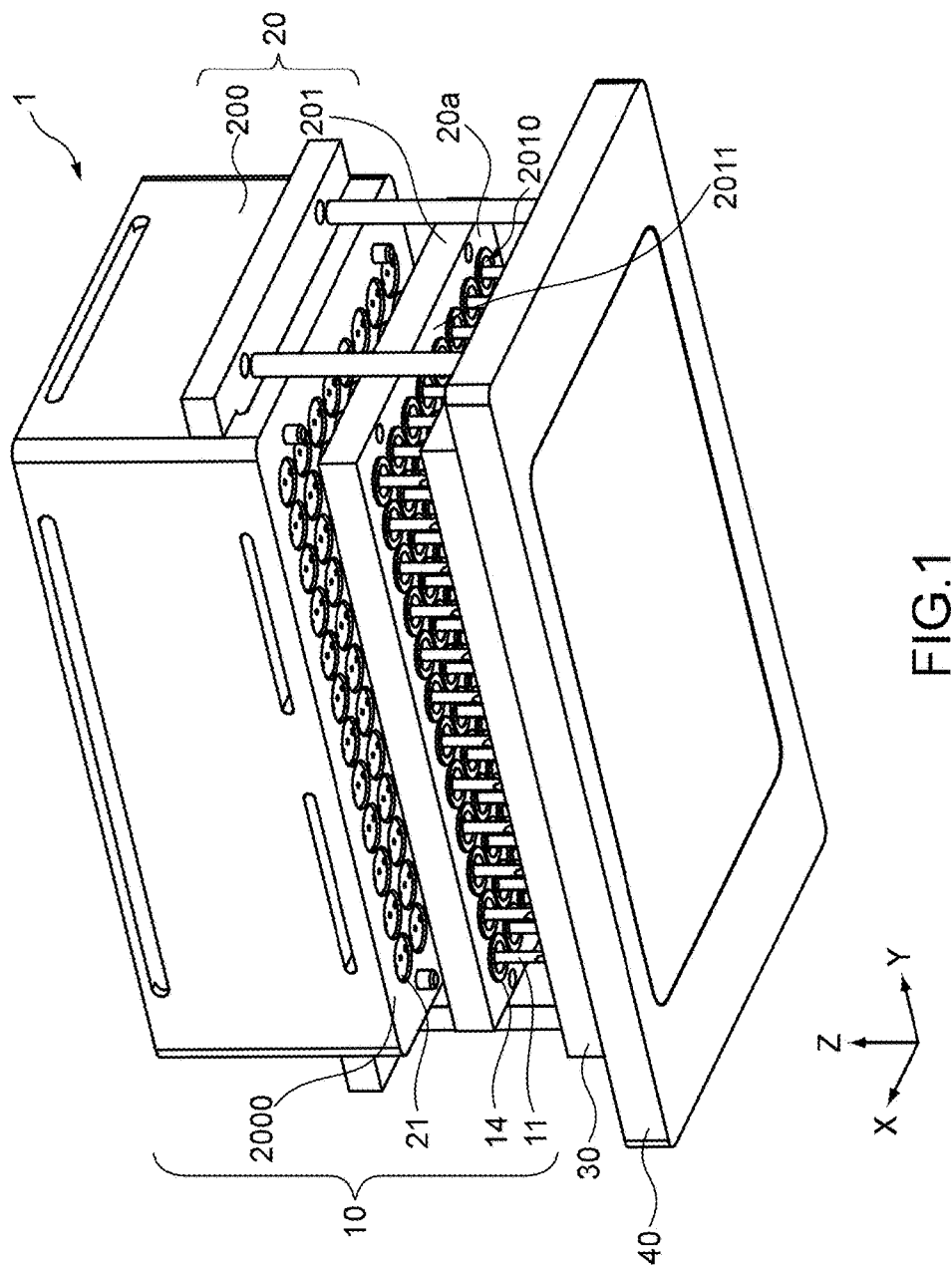
FIG. 1 is an exploded perspective view of a mixing device according to an embodiment of the present invention, showing a state of a multi-well plate installed therein.
Figure 2:
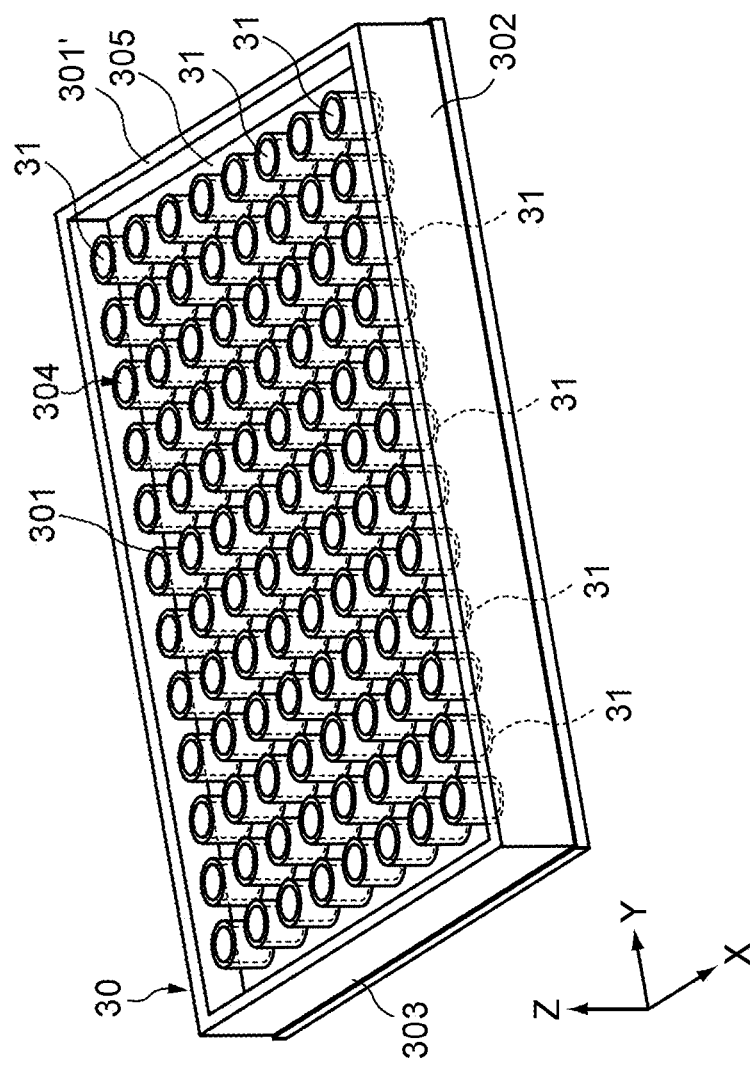
FIG. 2 is a perspective view of the multi-well plate installed in the mixing device.
Figure 3:
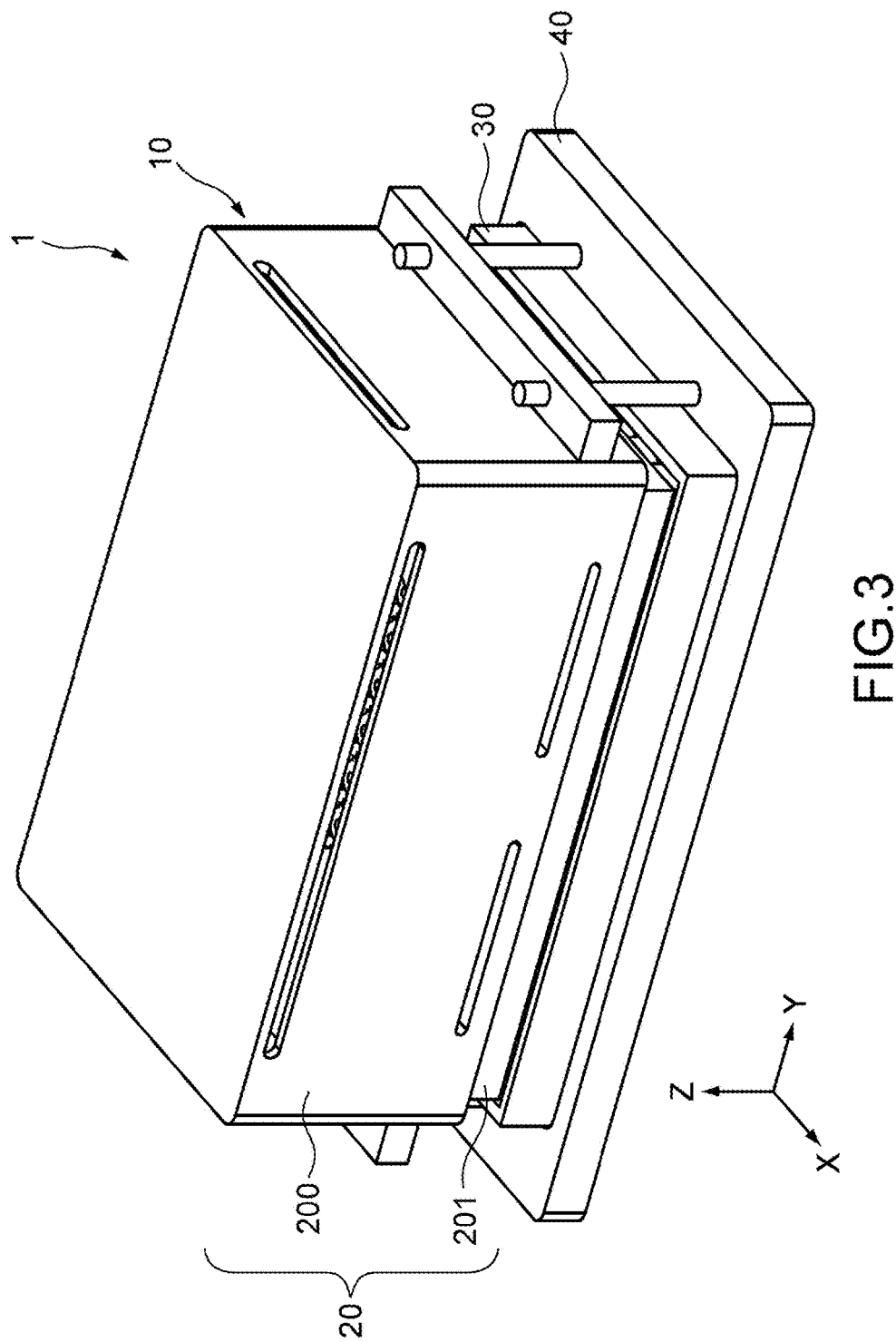
FIG. 3 is a perspective view showing a state of the mixing device during mixing.

FIG. 1 is an exploded perspective view showing a mixing device according to an embodiment of the present invention. FIG. 2 is a perspective view of a multi-well plate to be installed into the mixing device. FIG. 3 is a perspective view showing a state of the mixing device during mixing.

In each figure, X- and Y-axis directions represent horizontal directions orthogonal to each other and a Z-axis direction represents a height direction orthogonal to those directions.

[Overall Configuration]

As shown in FIGS. 1 and 3, a mixing device 1 of this embodiment includes a mixing unit 10, a mounting table 40, and a controller (not shown). The mounting table 40 is a table on which a multi-well plate 30 is placed in a horizontal plane (XY-plane). In a plan view, the mounting table 40 has a rectangular shape, the multi-well plate 30 also has a rectangular shape, and the mounting table 40 is larger than the multi-well plate 30.

The mixing device 1 is configured to be capable of installing therein the multi-well plate 30 including a plurality of wells 31. The plurality of wells 31 are capable of containing matter to be mixed. The mixing device 1 includes mixing mechanisms (represented by symbols 50 in FIG. 4). The mixing mechanisms are each provided in each of the wells 31 and mix the matter to be mixed by using motors 12. The mixing mechanisms individually placed corresponding to each well 31 have identical configurations.

As shown in FIG. 2, the multi-well plate 30 includes an approximately rectangular box-like member and the plurality of wells 31 each having a cylindrical shape. The box-like member includes a bottom surface 305, long-side side surfaces 302, and short-side side surfaces 303. The wells 31 are arranged in a matrix form on the bottom surface 305. The wells 31 have a plurality of cavities. The wells 31 include circular openings 304.

In order for the mixing device 1 to mix the matter to be mixed in the multi-well plate 30, upper surfaces 301 of circular edges forming the openings 304 of the wells 31 are brought into contact with a main surface portion 20a of a casing 20 that constitutes the mixing unit 10. The upper surfaces 301 are arranged, approximately flush with an upper surface 301' of a frame of the box-like member. The multi-well plate 30 is typically formed of an injection-molded, translucent synthetic-resin material or a cut glass or metal.

The plurality of wells 31 are arranged in a matrix at predetermined intervals. In the example of the figure, eight wells 31 arrayed in a short-side direction (X-axis direction) are arranged by twelve rows in a long-side direction (Y-axis direction), so that a total of 96 wells are formed. An arrangement interval for the wells 31 is approximately 9 mm. It should be noted that the number of wells is not limited to this example and may be 6, 24, 384, 1536, or the like and the arrangement interval appropriately depends on the number of wells.

In this embodiment, the box-like member in which the plurality of cylindrical wells 31 are formed is used as the multi-well plate 30. Alternatively, a plate-like member may be used as the multi-well plate 30 and a plurality of non-through-holes (with bottoms) serving as wells may be formed in one surface of the plate-like member.

For the multi-well plate 30, commercially available general-purpose products are typically used. For example, "Web Seal Plate+96-Well Glass-Coated Microplate" manufactured by Thermo Fisher Scientific K.K can be employed.

The mixing unit 10 includes the mixing mechanisms (represented by symbols 50 in FIG. 4) for mixing solution contained in the wells 31 of the multi-well plate 30. The mixing mechanism is provided for each well 31. The mixing mechanism includes a mixing rod 11 that mix solution in the well 31. The mixing mechanism will be described later in detail.

Driving of the mixing unit 10 is controlled by the controller (not shown). Typically, the controller includes a computer including a central processing unit (CPU), a memory (read only memory (ROM), and a random access memory (RAM)). The controller may include a general-purpose computer or may include a dedicated computer.

The controller is electrically connected to the mixing unit 10. The controller is configured to individually or commonly control rotation of the motors that drive the mixing rods 11. In this embodiment, the controller is electrically connected to the mixing unit 10 via a wiring member, though not limited thereto. For example, the controller may be wirelessly, electrically connected to the mixing unit 10.

[Mixing Unit]

Figure 4:
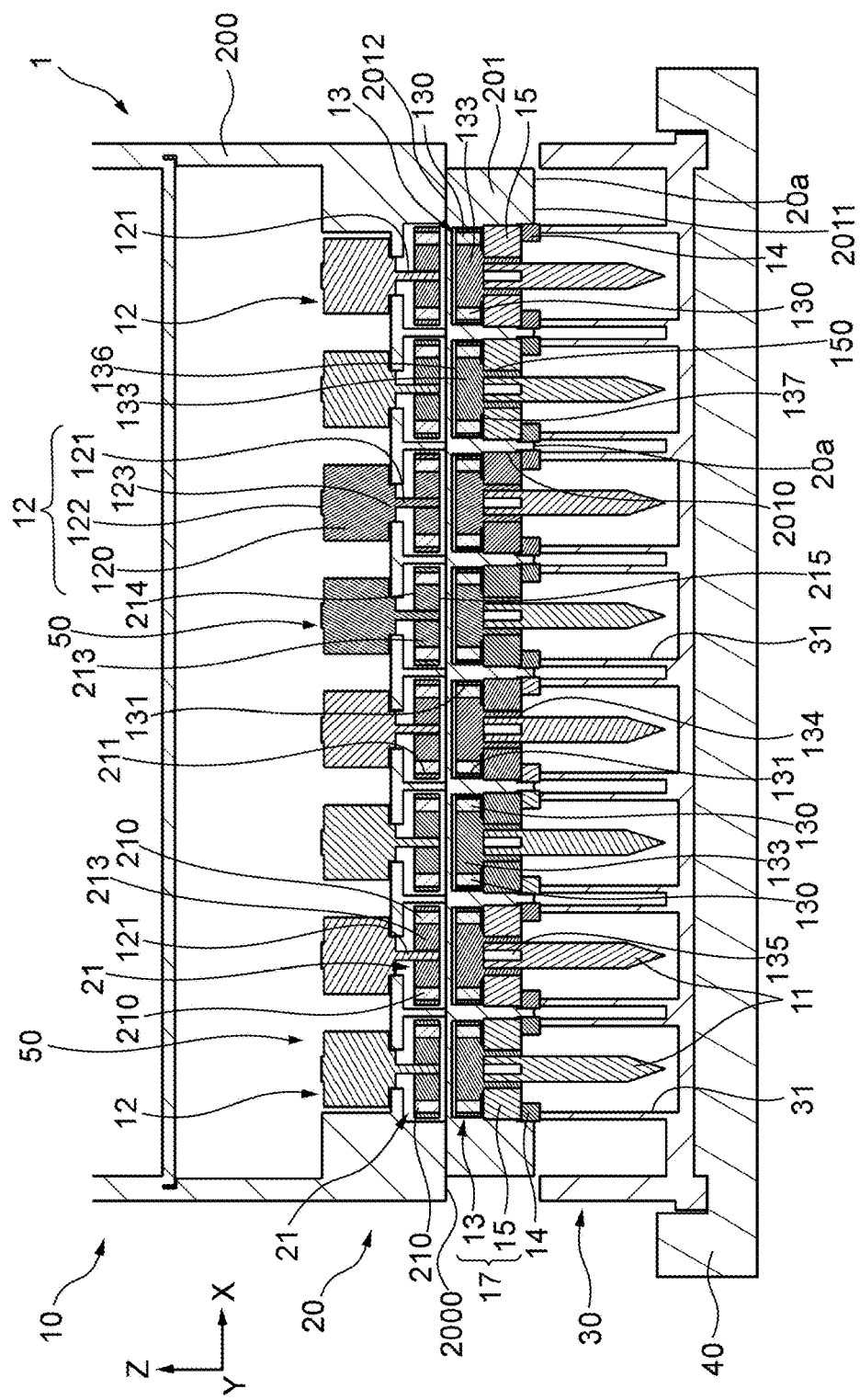
FIG. 4 is a partial, cross-sectional view of the mixing device in which the multi-well plate is installed.

Hereinafter, the mixing unit 10 including the mixing mechanisms will be described in detail with reference to FIGS. 1, 3, and 4. FIG. 4 is a partial, cross-sectional view of the mixing device 1 in which the multi-well plate 30 is installed. FIG. 4 corresponds to a partial, cross-sectional view of the mixing device of FIG. 3, which is taken in the X-axis direction.

The mixing unit 10 includes the casing 20 and the mixing mechanisms 50. The casing 20 includes the main surface portion 20a that is opposed to the upper surface 301' of the multi-well plate 30. The casing 20 houses the mixing mechanisms 50.

The casing 20 has a stacked structure of a motor-housing casing 200 and a housing 201. The motor-housing casing 200 retains first magnetic disks 21 and the motors 12. The first magnetic disks 21 are first rotators. The first magnetic disk 21 and the motor 12 form parts of the mixing mechanism 50 to be described later. The housing 201 retains second rotators 17 and seal rings 14. The second rotator 17 and the seal ring 14 form parts of the mixing mechanism 50 to be described later. The motor-housing casing 200 and the housing 201 are stacked in the Z-axis direction of the figure and form the casing 20. The motor-housing casing 200 and the housing 201 are separable from each other.

The motor-housing casing 200 is, for example, formed of a metal material such as an aluminum alloy. The motor-housing casing 200 has a bottom surface 2000 formed in an approximately rectangular plate-like shape which is adjacent to the housing 201. The plurality of first magnetic disks 21 are disposed in the bottom surface 2000 such that a second surface 215 of the first magnetic disk 21 corresponding to each well 31 is exposed.

The motor-housing casing 200 houses the motors 12, the first magnetic disks 21, and a circuit board (not shown) that drives the plurality of motors 12.

The housing 201 is formed of at least one of a polyetheretherketone (PEEK) resin, a fluorocarbon polymer, and a polyphenylene sulfide, for example, which are resistant to solvent and resistant to high heat. The housing 201 is formed of a PEEK resin in this embodiment. The housing 201 includes a first flat surface 2012 and a second flat surface 2011 opposed to the first flat surface 2012. The first flat surface 2012 is adjacent to the bottom surface 2000 of the motor-housing casing 200. The second flat surface 2011 of the housing 201 corresponds to the main surface portion 20a of the casing 20.

The housing 201 is formed in an approximately rectangular plate-like shape. A plurality of housing compartments 2010 are formed in the second flat surface 2011, each corresponding to each well 31. The housing compartments 2010 are non-through-holes (with bottoms). Each of the housing compartments 2010 houses and retains the second rotator 17, part of the mixing rod 11, and part of the seal ring 14. The second rotator 17 is magnetically coupled with the first magnetic disk 21. The seal ring 14 is disposed on a circumferential portion of an opening of the housing compartment 2010. The opening of the housing compartment 2010 is a circular opening disposed correspondingly to the opening 304 of the well 31. The seal ring 14 partially protrudes from the second flat surface 2011. Further, the mixing rod 11 protrudes from the second flat surface 2011 of the housing 201 toward the well 31.

The housing compartment 2010 of the housing 201 is formed in a non-through-hole shape. The first flat surface 2012 of the housing 201 is adjacent to the bottom surface 2000 of the motor-housing casing 200. The first flat surface 2012 of the housing 201 is interposed between the motor-housing casing 200 and the second rotators 17. Further, the second rotators 17, the mixing rods 11, and the seal rings 14 that form parts of the plurality of mixing mechanisms 50 each provided in each well 31 are partitioned by the housing 201 (housing compartments 2010) on a well-by-well basis and retained in a mutually isolated state.

In the mixing device 1, the mixing unit 10 and the mounting table 40 are separable from each other. The mixing unit 10 is movable with respect to the mounting table 40 in upper and lower directions (Z-axis direction). The multi-well plate 30 is placed on the mounting table 40 in a state in which the mixing unit 10 and the mounting table 40 are separated from each other by moving the mixing unit 10 in the upper direction. In mixing the matter to be mixed in the wells 31 after the multi-well plate 30 is placed on the mounting table 40, mixing is performed in a state in which the upper surfaces 301 that are the edges forming the openings of the wells 31 of the multi-well plate 30 placed on the mounting table 40 are held in contact with the seal rings 14 of the mixing unit 10 by moving the mixing unit 10 in the lower direction. Here, if a plate-like member is used as the multi-well plate and a plurality of non-through-holes (with bottoms) serving as wells are formed in one surface of the plate-like member, the upper surface of the multi-well plate is held in contact with the seal rings 14 of the mixing unit 10 and the second flat surface 2011 of the housing 201 during mixing.

In this manner, the first flat surface 2012 of the housing 201 is interposed between the first magnetic disks (first rotators) 21 that are driving rotators and the second rotators 17 that are driven rotators, and the first magnetic disks (first rotators) 21 are spatially isolated from the second rotators 17. The housing 201 is interposed between the motor-housing casing 200 in which the first magnetic disks (first rotators) 21 are housed and the second rotators 17. The housing 201 is also interposed between the mixing mechanisms 50 each arranged in each of the wells 31 adjacent to each other. With such a configuration, the motor-housing casing 200 can hold the housing 201 with the bottom surface 2000 during mixing. With this, pressure can be in-plane uniformly applied on the plurality of seal rings 14 each provided corresponding to each well 31. The air tightness of the plurality of wells 31 of the multi-well plate 30 can be enhanced without in-plane variations.

For example, there is a case where the housing is not interposed between the motor-housing casing and the second rotators, a casing in which the plurality of first rotators are arranged and retained in a matrix form and a casing in which the plurality of second rotators are arranged and retained in a matrix form are held at four corners of an outer periphery of each casing, and the first rotators are magnetically coupled with the second rotators. In this case, it is difficult to in-plane uniformly hold the casings together. Thus, holding of the multi-well plate at a center portion thereof weakens. Therefore, pressure applied on a seal corresponding to the well positioned at the center portion of the multi-well plate is lower than pressure applied on each of seals at other positions. Thus, the air tightness of the well positioned at the center portion of the multi-well plate is deteriorated.

In contrast, in this embodiment, the housing 201 (first flat surface 2012) is interposed between the second rotators 17 and the motor-housing casing 200 and also interposed between the individual second rotators 17. With such a configuration, the pressure can be in-plane uniformly applied on a plurality of seals during mixing and the air tightness in the plurality of wells 31 of the multi-well plate 30 can be in-plane uniformly enhanced.

Moreover, in this embodiment, mixing is performed in a state in which the mounting table 40 and the casing 20 sandwich the multi-well plate 30 at surfaces thereof. In the second flat surface 2011 of the housing 201 forming a part of the casing 20, i.e., a surface positioned on a side of the multi-well plate 30, the housing compartments 2010 that are the non-through-holes each provided in each well 31 and houses the second rotator 17 are formed. Therefore, the housing 201 is interposed between the individual second rotators 17 and also interposed between the second rotators 17 and the motor-housing casing 200. Then, the mounting table 40 has a rectangular plane shape that retains the entire bottom surface of the multi-well plate 30. Thus, the multi-well plate 30 can be held by the mounting table 40 and the casing 20 with in-plane uniform pressure. Thus, the air tightness in the plurality of wells 31 can be in-plane uniformly enhanced.

Further, the motor-housing casing 200 has a configuration in which the motor-housing casing is interposed between the individual first rotators (the first magnetic disks 21 and the motors 12). With this, it is possible to hold the housing upper surface with the surface of the motor-housing casing, and to inhibit deformation of the housing 201.

Further, even if the respective wells 31 of the multi-well plate 30 has variations in opening height, the variations in opening height can be overcome by the individual seal rings 14 because the seal rings 14 are individually provided in each well 31. Thus, the air tightness in the wells 31 can be made in-plane uniform.

As shown in FIGS. 1 and 4, regarding the mixing mechanisms 50, those having identical configurations are arranged in a matrix form in the casing 20, corresponding to all the wells 31 of the multi-well plate 30. Each of the mixing mechanisms 50 includes the motor 12, the first rotator 21, the second rotator 17, a magnetic coupling mechanism that magnetically couples the first magnetic disk (first rotator) 21 with the second rotator 17, the seal ring 14, and the mixing rod 11.

In the mixing mechanism 50, the first magnetic disk (first rotator) 21 that is the driving rotator is connected to the motor 12. Due to activation of the motor 12, the first magnetic disk 21 rotates. The first magnetic disk 21 and the second rotator 17 are coupled with each other by the magnetic coupling mechanism. The second rotator 17 rotates, following the first magnetic disk 21. The mixing rod 11 coupled with the second rotator 17 rotates due to the second rotator 17, and mixes the matter to be mixed in the well 31.

The motor 12 includes a motor chassis 120, a motor shaft 121, and two bearings 122 and 123.

The motor chassis 120 loads a rotor and a stator of the motor. The motor shaft 121 is connected to the rotor. The bearing 122 and the bearing 123 are fixed to the motor chassis 120 and supports the motor shaft 121 to be rotatable. The first magnetic disk 21 serving as the first rotator 21 is coupled with and supported by the motor shaft 121.

Lubricating grease is applied on the bearing 122 and the bearing 123. In this embodiment, the magnetic coupling mechanism is employed as the mixing mechanism. Therefore, the first magnetic disk 21 coupled with the motor 12 is spatially isolated from the second rotator 17 with which the mixing rod 11 is coupled. Therefore, vapor and the like of solution contained in the matter to be mixed does not reach the motor 12. Thus, the lubricating grease does not flow out or is not deteriorated due to the vapor and the like of the solution contained in the matter to be mixed.

The motor 12 functions as a drive unit that rotates the motor shaft 121 around an axis thereof. The rpm of the motor 12 is not particularly limited. In this embodiment, the rpm of the motor 12 can be set to fall within a range of 1 rpm to 6000 rpm, and a motor having accuracy of the rpm that is ±2% or less is used. With this, it is possible to handle both of low-speed mixing and high-speed mixing and to realize highly accurate control of the rpm of the mixing rod 11.

The motor 12 is a stepping motor driven with pulse signals, though not limited thereto. For example, a motor capable of accurately controlling the rpm such as a synchronous motor and a brushless DC motor can be employed. Also the size of the motor 12 is not particularly limited and, for example, the motor 12 having a diameter of 6 mm or less is used.

Each motor 12 is electrically connected to the circuit board (not shown) via a flexible wiring board (not shown). The circuit board is electrically connected to the controller (not shown) via the wiring member, and driving of each motor 12 is individually controllable by the controller. Each motor 12 is driven at identical rpm (rotation speed) in an identical direction of rotation, though not limited thereto. The direction of rotation and/or the rpm may be different for each motor. Further, all the motor 12 may be simultaneously activated or some of the motor 12 may be selectively activated. The circuit board may be placed inside the mixing device 1 or may be placed outside the mixing device 1.

Figure 5:
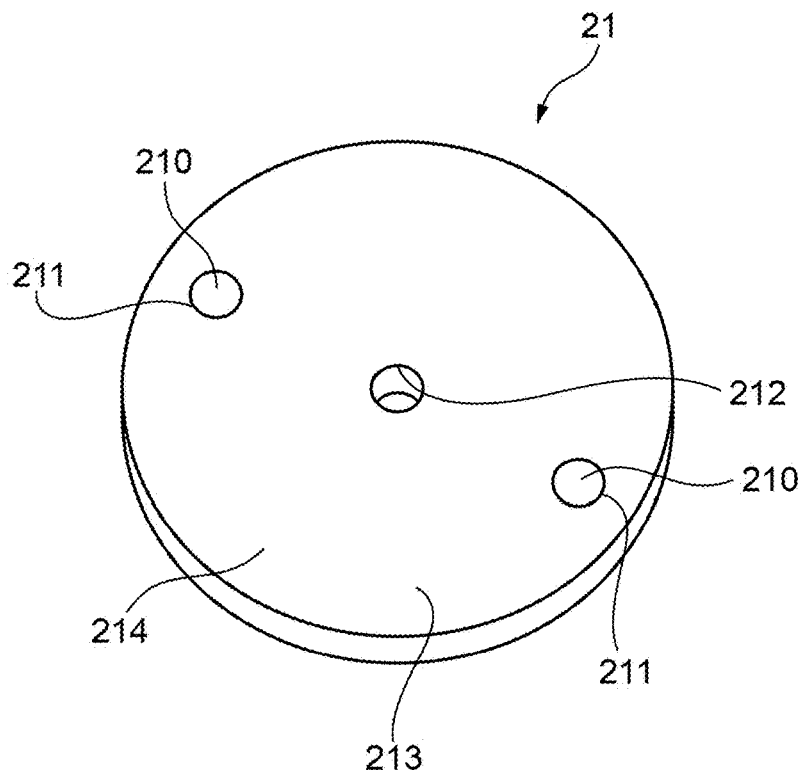
FIG. 5 is a perspective view of a magnetic disk that forms a part of a mixing mechanism of the mixing device.
Figure 6:
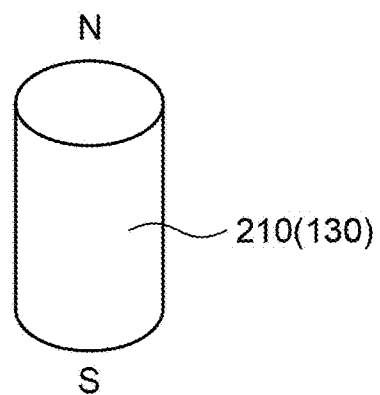
FIG. 6 is a perspective view of a first magnet (second magnet) that forms a part of the magnetic disk.
Figure 8:
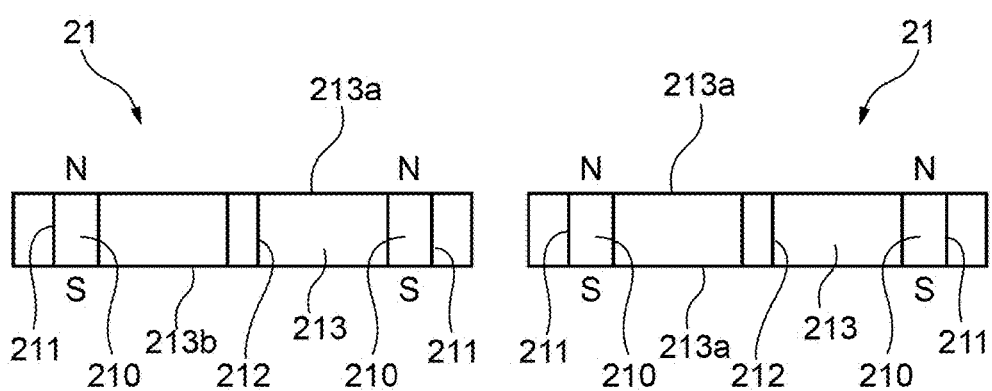
FIG. 8 is a schematic cross-sectional view of the magnetic disk.

FIG. 5 is a perspective view of the first magnetic disk 21 that is the first rotator. FIG. 6 is a perspective view of a magnet that forms a part of the magnetic disk 21. FIG. 8 is a view showing arrangement of magnetic poles of magnets to be incorporated in the first magnetic disks 21 of the two mixing mechanisms adjacent to each other.

As shown in FIGS. 4 and 5, the first magnetic disk 21 serving as the first rotator 21 includes a first-magnetic-disk main body 213 and two first magnets 210. The first magnetic disk 21 includes a first surface 214 and the second surface 215 disposed to be opposed to each other in a rotational-axis direction (Z-axis direction). The first surface 214 and the second surface 215 are disposed in parallel to the horizontal plane (XY-plane) such that the first surface 214 is located on the side of the motor 12 and the second surface 215 is located on the side of the second rotator 17.

As shown in FIGS. 4, 5, and 8, in the first-magnetic-disk main body 213 having a circular plate shape, a single through-hole 212 is formed at a center portion thereof and two through-holes 211 are formed in an outer periphery. The motor shaft 121 is inserted into the through-hole 212 formed at the center portion, and is supported therein. The first magnets 210 are inserted into the two through-holes 211 formed in the outer periphery.

Each of the through-holes 211 and 212 are formed in parallel to the motor shaft 121 that is a rotational shaft, extending from the first surface 214 toward the second surface 215. The two through-holes 211 provided in the outer periphery of the first-magnetic-disk main body 213 are disposed to be opposed to each other while sandwiching the through-hole 212 positioned at the center portion therebetween. Further, the two through-holes 211 are arranged in a diameter direction of the first-magnetic-disk main body 213.

As shown in FIG. 6, the first magnets 210 each have a columnar shape. As shown in FIGS. 4 and 8, the two first magnets 210 are disposed in such a manner that the two first magnets 210 are respectively inserted into the two through-holes 211. The first magnets 210 provided in the first magnetic disks 21 each include two different magnetic poles, specifically, an N-magnetic pole part indicated by the symbol N at one end thereof in a longitudinal direction and an S-magnetic pole part indicated by the symbol S at the other end. In this embodiment, when the first magnetic disk 21 is incorporated in the mixing device 1, the N-pole is located on the side of the first surface 214 located on the side of the motor 12 and the S-pole is located on the side of the second surface 215 located on the side of the second rotator 17.

As shown in FIG. 4, the second rotator 17 includes a second magnetic disk 13 and a bearing 15. The second magnetic disk 13 serves as a rotational portion that is the driven rotator. As in the first magnetic disk 21, the second magnetic disk 13 includes a second-magnetic-disk main body 133 having a circular plate shape, two second magnets 130, a hollow, cylindrical portion 134, and a rotational shaft 135. The second magnetic disk 13 includes a first surface 136 and a second surface 137. The first surface 136 and the second surface 137 are disposed to be opposed to each other in the rotational-axis direction (Z-axis direction).

Regarding the second-magnetic-disk main body 133 having a circular plate shape, two through-holes 131 are formed in an outer periphery thereof. The through-holes 131 are formed in parallel to the rotational shaft 135, extending from the first surface 136 toward the second surface 137. The two through-holes 131 are disposed to be opposed to each other while sandwiching the center of the second-magnetic-disk main body 133 therebetween. Further, the two through-holes 131 are arranged in a diameter direction of the second-magnetic-disk main body 133. The first-magnetic-disk main body 213 and the second-magnetic-disk main body 133 have the same outer diameter. When the first-magnetic-disk main body 213 is superimposed on the second-magnetic-disk main body 133, the positions of the through-holes 211 correspond to the positions of the through-holes 131.

As shown in FIG. 6, the second magnet 130 has a columnar shape as in the first magnet 210. The two second magnets 130 are disposed in such a manner that the two second magnets 130 are respectively inserted into the two through-holes 131. The second magnets 130 provided in the second magnetic disk 13 each include two different magnetic poles, specifically, an N-magnetic pole part indicated by the symbol N at one end thereof in a longitudinal direction and an S-magnetic pole part indicated by the symbol S at the other end. In this embodiment, when the second magnetic disk is incorporated in the mixing device 1, the N-pole is located on the side of the first surface 136 located on the side of the first magnetic disk 21 and the S-pole is located on the side of the second surface 137 located on the side of the well 31.

The magnetic coupling mechanism includes the two first magnets 210 and the two second magnets 130. A direction of magnetic coupling is the rotational-axis direction (Z-axis direction). As described above, the N-pole and the S-pole of each of the first magnet 210 and the second magnet 130, which are magnetically coupled with each other, are arranged in the direction of magnetic coupling. All the first magnets 210 and the second magnets 130 which are provided in the mixing mechanisms 50 each corresponding to each well 31 are arranged such that the N-poles are located on the upper side and the S-poles are located on the lower side in FIG. 4. It was found that non-uniformity of rotation of the mixing mechanisms 50 each corresponding to each well 31 during mixing is reduced when the first and second magnets 210 and 130 are arranged such that the directions of the magnetic poles of all the first and second magnets 210 and 130 provided in the mixing mechanisms 50 are the same in this manner. With this, substantially uniform mixing can be achieved in all the wells 31.

As a distance between the two first magnets 210 of the single first magnetic disk 21 becomes larger, it becomes easier to transmit torque. However, step-out becomes more likely to occur and further, interference between the first magnetic disks 21 adjacent to each other becomes stronger. Therefore, it is desirable to appropriately adjust and optimize the value of the distance between the two first magnets 210 of the single first magnetic disk 21. In this embodiment, the distance between the two first magnets 210 provided in the single first magnetic disk 21 is set to 6 mm. Note that the diameter of the first magnetic disk 21 is 8 mm, the diameter of the first magnet 210 is 1 mm, and a distance between the centers of the first magnetic disks 21 adjacent to each other is 9 mm. The same applies to the second magnets 130 and the second magnetic disk 13. The diameter of the second magnetic disk 13 does not need to be completely identical to that of the first magnetic disk 12 as long as a magnet-to-magnet distance of the two magnets provided in the second magnetic disk 13, the diameter of the magnet, and the distance between the centers of the second magnetic disks 13 adjacent to each other are identical to those of the first magnetic disk 12.

Further, as a distance between the first magnet 210 and the second magnet 130 becomes smaller, it becomes easier to transmit torque. However, if the distance between the first magnet 210 and the second magnet 130 is too small, the attraction between the magnetic disks of both becomes excessively strong, and heavy load is applied on the bearing 15 and the motor 12. Therefore, it is desirable to appropriately adjust and optimize the value of the distance between the first magnet 210 and the second magnet 130. In this embodiment, the distance between the first magnet 210 and the second magnet 130 is set to 1 to 2 mm.

Further, it is desirable to appropriately adjust the distance between the motor 12 and the first magnetic disk 21 so as to inhibit influence of leakage of a magnetic flux from the motor 12. The distance between the motor 12 and the first magnetic disk 21 is desirably set to approximately 2 mm to 6 mm. In this embodiment, the distance between the motor 12 and the first magnetic disk 21 is set to 4.2 mm.

The cylindrical portion 134 is disposed at a center portion of the second surface 137 of the second-magnetic-disk main body 133. The cylindrical portion 134 is coupled with the second surface 137 such that a longitudinal direction of the cylindrical portion 134 is orthogonal to the second surface 137. The cylindrical portion 134 has a cavity. The mixing rod 11 is inserted into and supported in this cavity. Moreover, the rotational shaft 135 is disposed at the center of the hollow, cylindrical portion 134. The rotational shaft 135 is coupled with the second surface 137 so as to be orthogonal to the second surface 137. The rotational shaft 135 is inserted into a rotational shaft insertion hole formed at one end of the mixing rod 11 having a pole shape. The rotational shaft 135 is configured such that the mixing rod 11 rotates, following rotation of the rotational shaft 135. The mixing rod 11 is coupled with the second magnetic disk 13 through the cylindrical portion 134 and the rotational shaft 135.

The second-magnetic-disk main body 133 and the cylindrical portion 134 are formed of a resin or the like by integral injection molding, for example. Examples of the material therefor can include a PEEK resin, a fluorocarbon polymer, and a polyphenylene sulfide, which are excellent in resistance to solvent.

The motor shaft 121 and the rotational shaft 135 of the second magnetic disk 13 are arranged on the same axis. The rotational shaft 135 of the second magnetic disk 13 serving as the rotational portion is coupled with the mixing rod 11. The mixing rod 11 is provided such that a longitudinal direction of the mixing rod 11 is positioned on the same axis with the motor shaft 121 and the rotational shaft 135.

Figure 7:
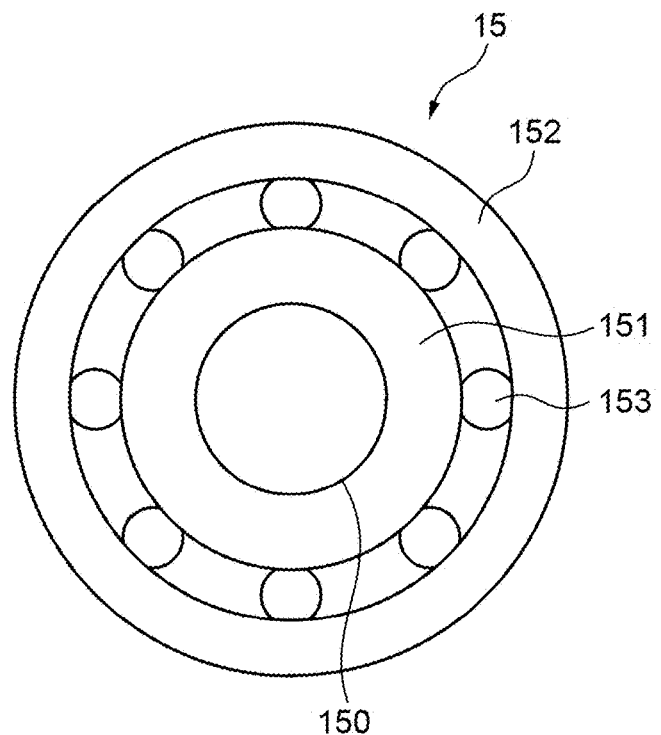
FIG. 7 is a plan view of a bearing that forms a part of the mixing mechanism of the mixing device.

The bearing 15 is provided between the second magnetic disk 13 and the seal ring 14. FIG. 7 is a plan view of the bearing 15. As shown in FIG. 7, the bearing 15 includes an inner race 151, an outer race 152, a plurality of balls 153, and a retainer (not shown). The inner race 151 has a ring shape including a through-hole 150 at a center portion thereof. As shown in FIG. 4, the cylindrical portion 134 of the second magnetic disk 13, which supports the mixing rod 11, is inserted into the through-hole 150. The mixing rod 11 is coupled with the rotational shaft 135. The mixing rod 11 and the rotational shaft 135 are inserted into the through-hole 150. The outer race 152 has a ring shape including an inner diameter and an outer diameter which are larger than an outer diameter of the inner race 151. The outer race 152 is retained on an inner peripheral surface of the housing compartment 2010. The balls 153 are provided and retained between the inner race 151 and the outer race 152 to be capable of rolling. The retainer arranges the balls 153 at appropriate positions in constant intervals.

The bearing 15 is formed of at least one of a PEEK resin, a fluorocarbon polymer, and a polyphenylene sulfide, for example, which are resistant to solvent and resistant to high heat. In this embodiment, the bearing 15 is formed of a PEEK resin. A solid-state lubricant is used as a lubricant for the bearing 15. In addition to the solid-state lubricant, examples of the lubricant includes a lubricating grease. However, with the lubricating grease, there is a possibility that the lubricating grease may flow out due to the vapor and the like of the solution of the matter to be mixed in the well 31, which may contaminate the matter to be mixed. In this embodiment, the solid-state lubricant is used as the lubricant, and hence the contamination problem caused by the lubricating grease is avoided. The solid-state lubricant are classified into a soft-metal-based lubricant, a layered crystalline material, and a polymer-based lubricant. In this embodiment, a polymer-based lubricant is used as the lubricant and a polymer-based PEEK resin is used for the materials of the inner race 151, the outer race 152, and the retainer. Note that, in addition to the use of the polymer-based material for the materials of the inner race 151, the outer race 152, and the retainer, rolling contact surfaces of the inner race and the outer race, the retainer, and the balls using an alloy, for example, may be coated with a polymer-based material such as a fluorocarbon polymer for lubrication.

The magnetic coupling mechanism that magnetically couples the first magnetic disk 21 with the second rotator 17 includes the first magnets 210 provided in the first magnetic disk 21 and the second magnets 130 provided in the second magnetic disk 13 of the second rotator 17. The first magnetic disk 21 and the second rotator 17 are coupled with each other through the contactless, magnetic coupling mechanism, and transmit rotational driving force of the motor 12 to the second rotator 17 through the magnetic coupling mechanism. The mixing rod 11 is thus rotated.

In this embodiment, the two magnets are provided in each of the first magnetic disk 21 and the second magnetic disk 13, though not limited thereto. Further, the pole-like magnets are used in this embodiment, though the shape of the magnet is not limited thereto. For example, the plane shape of the magnet may be a cylindrical shape having a ring-like cavity.

Each of the seal rings 14 is provided for each well 31. The seal ring 14 serving as packing is formed in a ring shape surrounding the opening 304 of the well 31. It is desirable to use a material excellent in resistance to solvent as the material of the seal ring 14. An elastic material such as a fluorocarbon polymer and a fluorocarbon rubber is desirably used. In this embodiment, FFKM (tetrafluoroethylene-perfluoro(methylvinylether) rubber) is used.

Figure 9:
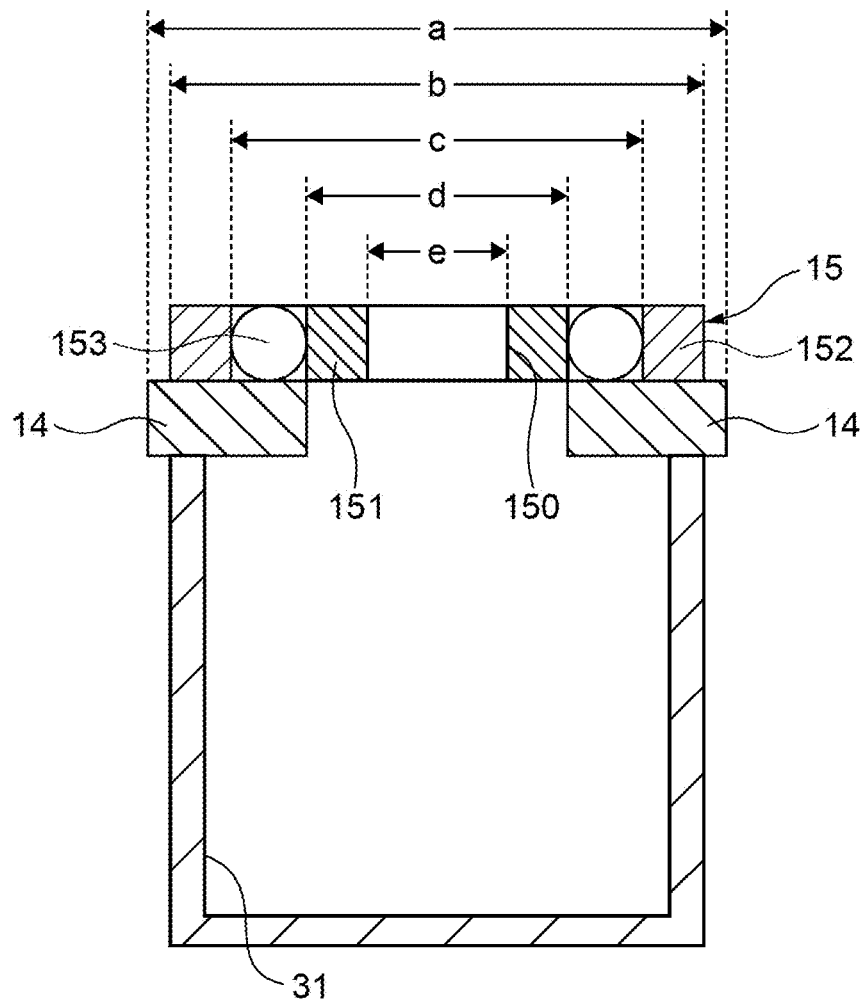
FIG. 9 is a partial, schematic cross-sectional view of the mixing device, showing a positional relationship among a well, a seal ring, and the bearing.

FIG. 9 is a cross-sectional view showing a positional relationship among the well 31, the seal ring 14, and the bearing 15. As shown in FIG. 9, the seal ring 14 is formed in a ring shape surrounding the opening 304 of the well 31. An inner diameter of the seal ring 14 is set to be smaller than the diameter of the opening 304 of the well 31 having a circular plane shape. Moreover, the inner diameter of the seal ring 14 is set to be approximately the same as the outer diameter of the ring-like inner race 151 of the bearing 15 or set to be smaller than the outer diameter of the inner race 151. In other words, the inner diameter of the seal ring 14 is set to be equal to or smaller than the outer diameter of the inner race 151 as the seal ring 14 and the inner race 151 are projected onto a plane orthogonal to the rotational shaft 135. In this embodiment, the inner diameter of the seal ring 14 is set to be smaller than the outer diameter of the inner race 151.

For example, in this embodiment, an inner diameter e of the inner race 151 is 3.0 mm, an outer diameter d of the inner race 151 is 4.95 mm, an inner diameter c of the outer race 152 is 6.75 mm, an outer diameter of the outer race 152, i.e., an outer diameter b of the bearing 15 is 8 mm, and an outer diameter a of the seal ring 14 is 8.5 mm.

By setting the inner diameter of the seal ring 14 to be equal to or smaller than the outer diameter of the inner race 151 in this manner, even if the inner race 151 is abraded by the balls of the bearing in long-term use and abrasion debris is produced due to this abrasion, the abrasion debris can be received by the seal ring 14 and inhibited from entering the well 31. As described above, resins are used for the materials of the inner race 151, the outer race 152, and the retainer in this embodiment, and hence abrasion debris is easily produced due to abrasion in long-term use. In this embodiment, the provision of the seal ring 14 inhibits abrasion debris from entering the well 31.

One end of the mixing rod 11 is coupled with the rotational shaft 135. Moreover, the one end of the mixing rod 11 is inserted into and supported in the cylindrical portion 134 of the second magnetic disk 13. The cylindrical portion 134 of the second magnetic disk 13, which supports the mixing rod 11, is inserted into the through-hole 150 of the bearing 15. The other end of the mixing rod 11 is a paddle portion. This paddle portion mixes the matter to be mixed in the well 31. Note that the shape of the paddle portion is not particularly limited and various shapes can be employed as long as a desired function of mixing the matter to be mixed is obtained due to rotation around the axis of the rotational shaft 135.

The mixing rod 11 is formed of at least one of a PEEK resin, a fluorocarbon polymer, and a polyphenylene sulfide, for example, which are resistant to solvent and resistant to high heat. In this embodiment, the mixing rod 11 is formed of a PEEK resin.

As shown in FIG. 4, the mixing rods 11 are disposed inside the respective wells 31 when the multi-well plate 30 is housed in the mixing device 1. Typically, each mixing rod 11 is located on a central axis of each well 31. The height of the mixing rod 11 from the bottom of the well 31 is not particularly limited and appropriately set in accordance with the size of the well 31, the amount and type of solution that is matter to be mixed, and the like. Typically, the height of the mixing rod 11 is set such that the tip of the mixing rod 11 is not in contact with the bottom of the well 31.

The plurality of mixing rods 11 are arranged in a matrix form in the casing 20, corresponding to all the wells 31 of the multi-well plate 30. The plurality of mixing rods 11 are each disposed inside each well 31, protruding from the main surface portion 20a toward the multi-well plate 30.

In the mixing unit 10, the arrangement interval and the like of the mixing rod 11 and the motor 12 are optimized in a manner that depends on the kind of the multi-well plate (or the number of wells) to be used.

[Operation of Mixing Device]

Next, a typical operation of the mixing device 1 configured as described above will be described.

First of all, the multi-well plate 30 with the matter to be mixed contained in each well 31 is placed on the mounting table 40. Next, the mixing unit 10 is moved in the lower direction, such that the mixing unit 10 is held in contact with the upper surfaces 301 of the edges forming the openings 304 of the wells 31 of the multi-well plate 30. Then, the first magnetic disks (first rotators) 21 and the second magnetic disks 13 of the second rotators 17 are magnetically coupled with one another due to the magnetic coupling mechanisms. With this, each mixing rod 11 is disposed inside each well 31 of the multi-well plate 30.

At this time, the seal ring 14 disposed on the main surface portion 20a of the casing 20 for each well 31 is held in close contact with the upper surface 301 of the edge of the opening 304 of each well 31 of the multi-well plate 30. The opening 304 of each well 31 is sealed by the second rotator 17 and the seal ring 14. Thus, the air tightness of a space surrounded by the well 31, the seal ring 14, and the second rotator 17 is enhanced. With this, evaporation of the solution in the well 31 is reduced. Further, a gap between the plurality of wells 31 adjacent to each other is blocked by a partition wall formed by the housing 201, the seal rings 14, and the second rotators 17. Thus, splashes of the matter to be mixed are inhibited from entering other wells 31 during mixing.

The controller outputs a drive pulse signal to the motor 12 and controls the motor 12 to rotate the mixing rod 11, which is disposed in the well 31 containing solution to be mixed, at predetermined rpm (e.g., 1000 rpm) Typically, the controller performs control to rotate each of the mixing rods 11 at the same rpm. Alternatively, the controller may perform control to rotate the mixing rods 11 at rpm different for each of the wells. Furthermore, the controller may simultaneously activate the motors or may activate the motors in predetermined order.

In this embodiment, a space inside the well 31 in which the mixing rod 11 is housed and a space in which the motor 12 serving as a driving source that rotates the mixing rod 11 is housed are isolated from each other by the magnetic coupling mechanism. Therefore, the solution contained in the matter to be mixed in the well 31 does not evaporate and reach the motor 12. Further, the air tightness in the well 31 is enhanced due to the seal ring 14 and the second rotator 17 is enhanced. Therefore, evaporation of the solution contained in the matter to be mixed in the well 31 is reduced. Thus, the concentration of a sample that is the matter to be mixed does not change.

Further, during mixing, insides of the wells 31 are completely isolated by the second rotators 17 and the seal rings 14 on a well-by-well basis. Therefore, vapor of the solution contained in the matter to be mixed in the well 31 is inhibited from being diffused and mixed into the matter to be mixed in another well.

Further, the pressure is in-plane uniformly applied on the seal rings 14 due to the housing 201. Therefore, the air tightness of the plurality of wells 31 can be kept in-plane uniform. Further, in-plane variations such as variations in concentration of samples, which depend on the positions of the wells 31, are reduced and highly accurate mixing can be performed.

Further, since the mixing rods 11 are driven by the respective motors 12, each of the mixing rods 11 can be rotated under optimal and appropriate driving conditions. Further, since each of the motors 12 is a stepping motor that can achieve accurate rpm with a drive pulse, mixing accuracy and mixing efficiency of the solution in each well 31 can be improved.

As described above, in accordance with this embodiment, it is possible to reduce evaporation of the solution contained in the matter to be mixed in each well 31, and to greatly enhance the mixing accuracy and the mixing efficiency of each well 31. Further, in accordance with this embodiment, it is possible to make the air tightness in each well 31 substantially uniform in plane during mixing, and to achieve uniform mixing irrespective of the positions of the wells 31. Therefore, in tests such as ELISA, the concentration of antibodies or antigens contained in a sample can be accurately detected or quantified.

Hereinabove, the embodiment of the present invention has been described, though the present invention is not limited to this embodiment. Various modifications can be made without departing from the gist of the present invention as a matter of course.

For example, the multi-well plate 30 with the 96 wells is used in the above-mentioned embodiment, though not limited thereto. Other multi-well plates with a different number of wells may be used. In this case, the arrangement pitches of the mixing rods, the size of the mounting table, and the like are optimized in a manner that depends on the outer shape of the multi-well plate and the arrangement pitches of the wells.

In order to further enhance the accuracy of the rpm of the mixing rod 11, the controller may be capable of monitoring the rpm of each mixing rod 11. In this case, for example, a detector such as an encoder that detects the rpm of the mixing rod 11 is provided in the casing and the controller is configured to control the mixing rod 11 to rotate at predetermined rpm on the basis of the output of the detector.

Further, in the above-mentioned embodiment, the plurality of motors 12 disposed corresponding to the plurality of mixing rods 11 are used as the drive units. Alternatively, a single motor may be configured to rotate the plurality of mixing rods 11.

Moreover, in the above-mentioned embodiment, the magnetic coupling mechanism includes the two first magnets 210 and the two second magnets 130, though not limited thereto. The magnetic coupling mechanism may include one magnet or three or more magnets as each of the first and second magnets 210 and 130. Each of the first and second magnets 210 and 130 is also not limited to the columnar shape, and may have a prism shape or a flat plate-shape.

Figure 10:
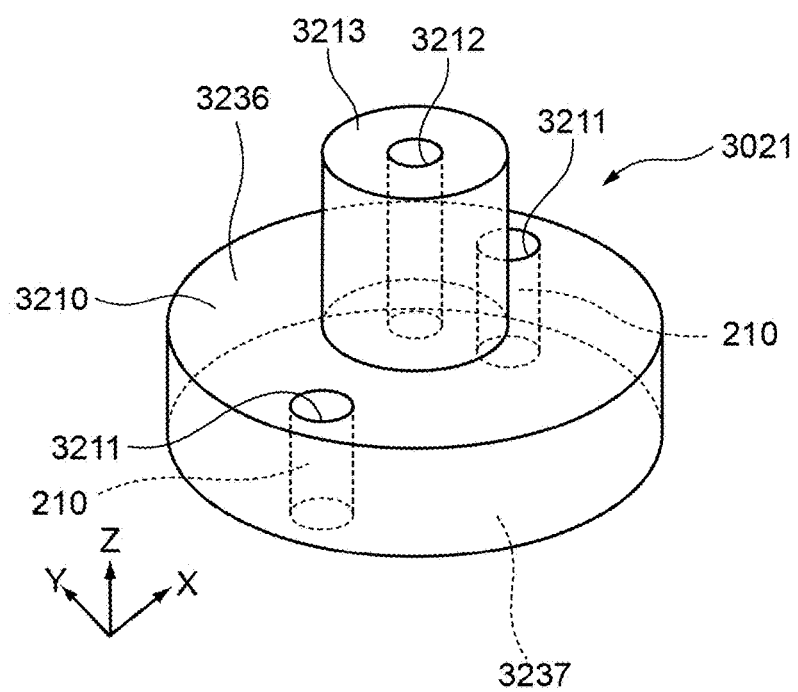
FIG. 10 is a perspective view of a first magnetic disk according to another embodiment of the present invention.
Figure 11:
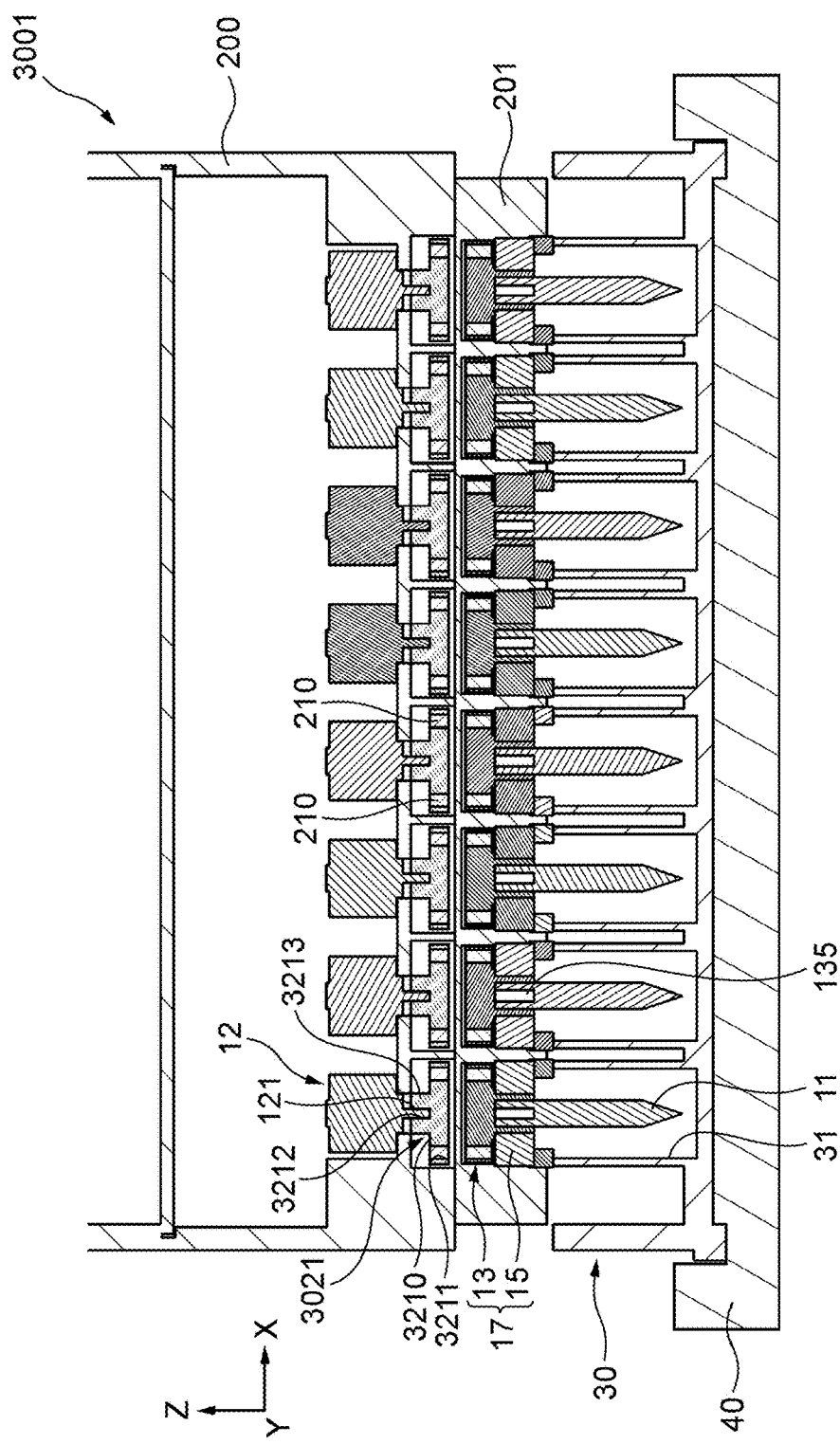
FIG. 11 is a partial, cross-sectional view of the mixing device in which the first magnetic disk shown in FIG. 10 is incorporated.

Further, the first magnetic disk 21 may have a structure shown in FIG. 10. FIG. 10 is a perspective view of a first magnetic disk 3021 that is another embodiment. FIG. 11 is a partial, cross-sectional view of a mixing device 3001 in which this first magnetic disk 3021 is incorporated. The mixing device 3001 is different from the mixing device 1 according to the above-mentioned embodiment only in that the structure of the first magnetic disk is different. Structures of the mixing device 3001 which are similar to those of the mixing device 1 will be denoted by similar symbols and descriptions thereof will be omitted.

As shown in FIGS. 10 and 11, the first magnetic disk 3021 includes a first-magnetic-disk main body 3210 having a circular plate shape, two first magnets 210, and a hollow, cylindrical portion 3213. The first magnetic disk 3021 includes a first surface 3236 and a second surface 3237 that are disposed to be opposed to each other in a rotational-axis direction (Z-axis direction).

In the first-magnetic-disk main body 3210 having a circular plate shape, two through-holes 3211 are formed at an outer periphery thereof. The through-holes 3211 are formed in parallel to a motor shaft 121 to be described later, extending from the first surface 3236 toward the second surface 3237. The two through-holes 3211 are formed at positions symmetrical with respect to the center of the first-magnetic-disk main body 3210. The two through-holes 3211 are arranged in a diameter direction of the first-magnetic-disk main body 3210. The two first magnets 210 are disposed in such a manner that the two first magnets 210 are respectively inserted into the two through-holes 3211.

The cylindrical portion 3213 is disposed at a center portion of the first surface 3236 of the first-magnetic-disk main body 3210. The cylindrical portion 3213 is coupled with the first surface 3236 such that a longitudinal direction of the cylindrical portion 3213 is orthogonal to the first surface 3236. The cylindrical portion 3213 has a cavity. The motor shaft 121 is inserted into and supported in this cavity.

By providing the cylindrical portion 3213 in this manner, a distance between the first magnet 210 and a motor 12 in the Z-axis direction increases by an amount corresponding to the height of the cylindrical portion 3213, and the first magnet 210 and the motor 12 can be retained, spaced apart from each other. With this, the magnetic coupling mechanism is hardly affected by a magnetic field leaking from the motor 12. Therefore, favorable mixing operations can be obtained.

Figure 12:
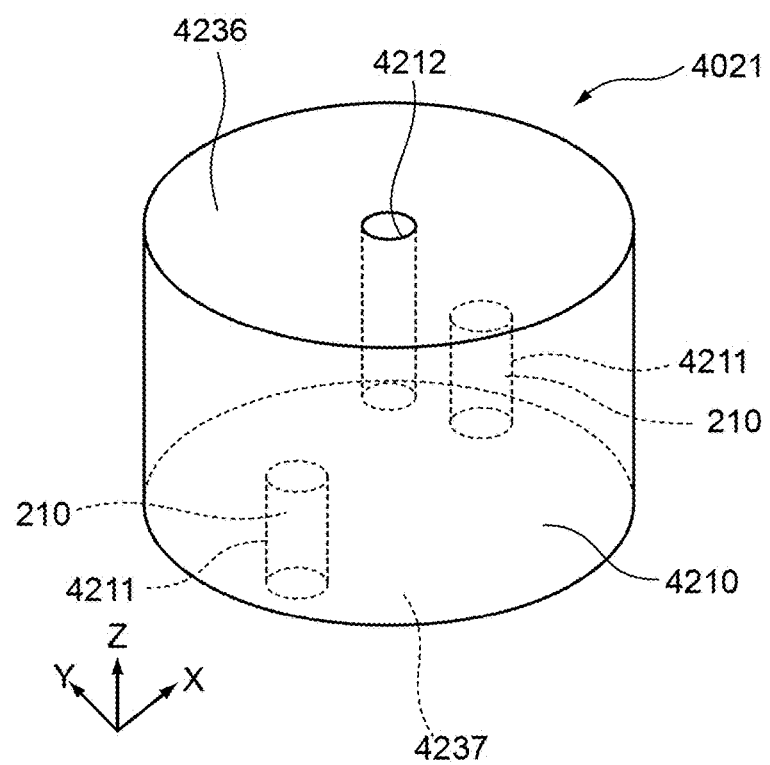
FIG. 12 is a perspective view of the first magnetic disk according to still another embodiment of the present invention.
Figure 13:
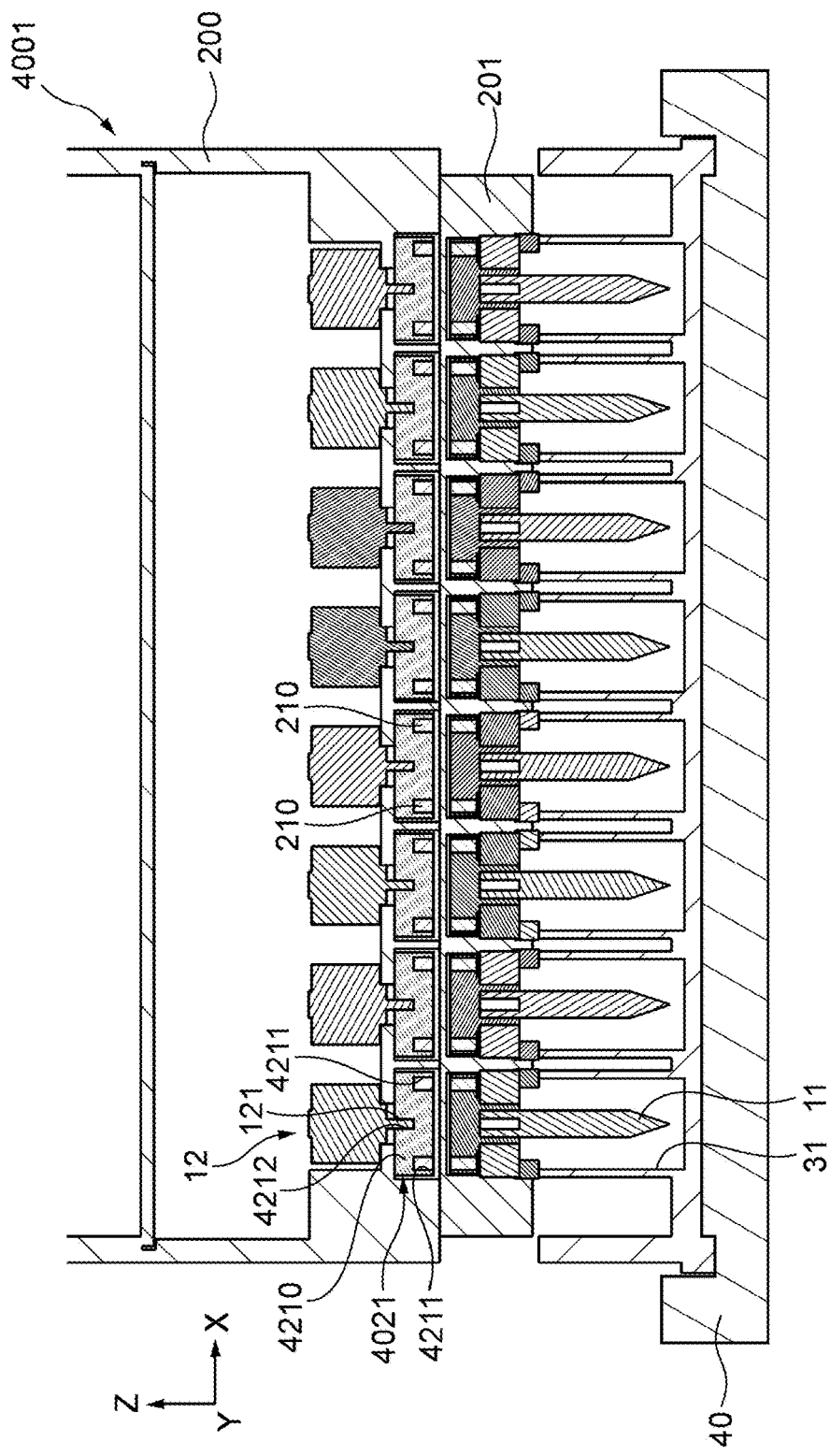
FIG. 13 is a partial, cross-sectional view of the mixing device in which the first magnetic disk shown in FIG. 12 is incorporated.

Further, in order to cause the first magnet 210 and the motor 12 to be spaced apart from each other, the first magnetic disk 21 may have a structure as shown in FIG. 12. FIG. 12 is a perspective view of a first magnetic disk 4021 that is still another embodiment. FIG. 13 is a partial, cross-sectional view of a mixing device 4001 in which this first magnetic disk 4021 is incorporated. The mixing device 4001 is different from the mixing device 1 according to the above-mentioned embodiment only in that the structure of the first magnetic disk is different. Structures of the mixing device 4001 which are similar to those of the mixing device 1 will be denoted by similar symbols and descriptions thereof will be omitted.

As shown in FIGS. 12 and 13, the first magnetic disk 4021 includes a first-magnetic-disk main body 4210 having a columnar shape and two first magnets 210. The first magnetic disk 4021 includes a first surface 4236 and a second surface 4237 that are disposed to be opposed to each other in a rotational-axis direction (Z-axis direction).

In the second surface 4237 of the first-magnetic-disk main body 4210 having a columnar shape, two non-through-holes 4211 are formed at an outer periphery thereof. The non-through-holes 4211 are formed in parallel to a motor shaft 121 to be described later. The two non-through-holes 4211 are disposed to be opposed to each other while sandwiching the center of the first-magnetic-disk main body 4210 therebetween. The two non-through-holes 4211 are arranged in a diameter direction of the first-magnetic-disk main body 4210. The two first magnets 210 are disposed in such a manner that the two first magnets 210 are respectively inserted into the two non-through-holes 4211.

In the first surface 4236 of the first-magnetic-disk main body 4210 having a columnar shape, a single non-through-hole 4212 is formed at a center portion thereof. The motor shaft 121 is inserted into and supported in the non-through-hole 4212.

By employing the columnar, first magnetic disk 4021 having a thickness in the Z-axis direction as shown in the figure, the first magnetic disk 4021 is positioned so as to fill a space extending in the Z-axis direction from the motor 12 to surfaces of the columnar, first magnets 210, which are opposed to surfaces of the first magnets 210, which are located on the side of the second surface 4237. Therefore, the first magnet 210 and the motor 12 can be retained, spaced apart from each other. With this, the magnetic coupling mechanism is hardly affected by a magnetic field leaking from the motor 12. Therefore, favorable mixing operations can be obtained.

Further, in the above-mentioned embodiment, the outer race 152 may be retained by press-fitting the outer race 152 of the bearing 15 into the housing compartment of the housing 201. Alternatively, the outer race 152 of the bearing 15 may be retained in the housing 201 by clearance fit.

If the bearing 15 is retained in the housing 201 by clearance fit, the outer diameter of the seal ring 14 is set to be larger than an opening diameter of the housing compartment into which the bearing 15 is inserted and the outer diameter of the outer race 152 of the bearing 15 is set to be smaller than the opening diameter of the housing compartment into which the bearing 15 is inserted.

The second rotator 17 is retained by the seal ring 14 and the housing 201 due to force of the seal ring 14 to press the housing 201 at the surface at which the seal ring 14 and the housing 201 are held in contact with each other.

The seal rings 14 is an elastic material having an O-ring shape.

The opening diameter of the housing compartment of the housing 201 into which the bearing 15 is inserted is 8.3 mm, the outer diameter of the seal ring 14 is 8.5 mm, and the outer diameter of the outer race 152 is 8 mm, for example.

By retaining the outer race 152 of the bearing 15 in the housing 201 by clearance fit as described above, the bearing 15 liable to be abraded in long-term operation and the mixing rod 11 that is an expendable product can be easily replaced.

Further, in the mixing device 1 of the above-mentioned embodiment, the mounting table 40 on which the multi-well plate 30 is placed is provided with a plurality of positioning bars extending in the Z-axis direction and the motor-housing casing 200 is provided with a plurality of through-holes into which the positioning bars are inserted. By inserting the positioning bars into the through-holes, the multi-well plate 30 and the motor-housing casing 200 can be positioned.

As described above, the mixing device 1 with the mounting table 40 and a mixing device without a mounting table are both possible.

With the mixing device without the mounting table, a multi-well plate, a housing, and a motor-housing casing, which are separable from one another, can be stacked, for example.

In this mixing device, the multi-well plate includes a plurality of screw holes in a peripheral portion of a surface in which well openings are formed.

The housing is a mixing module with a plurality of second rotators and includes a plurality of screws serving as positioning pins.

The motor-housing casing is a motor module with a motor.

The housing is stacked on the multi-well plate, and the screws provided in the housing are inserted into the screw holes of the multi-well plate and fixed. The multi-well plate and the housing can be thus positioned and fixed. The motor-housing casing is stacked on the multi-well plate and housing fixed to each other while the motor-housing casing is positioned with the positioning pins, and it can be used as the mixing device.

Figure 14:
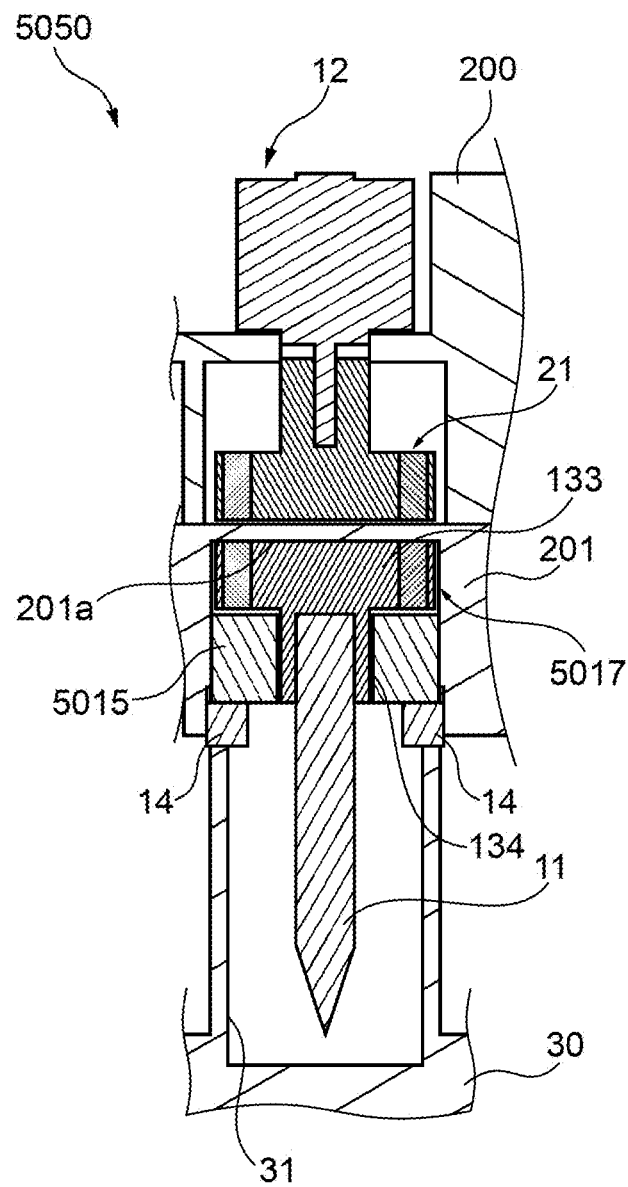
FIG. 14 is a cross-sectional view of the mixing mechanism including a second rotator according to a modified example.

Further, the ball bearing is used in the mixing mechanism 50 of the mixing device 1 of the above-mentioned embodiment. In contrast, a mixing mechanism 5050 including a slide bearing as shown in FIG. 14 may be employed as a modified example of the mixing mechanism. In the mixing mechanism 5050 shown in FIG. 14, a ring member 5015 serving as the slide bearing is disposed at the position at which the bearing 15 as the ball bearing of the above-mentioned embodiment would be disposed.

FIG. 14 is a cross-sectional view of the mixing mechanism 5050 as a modified example.

As shown in FIG. 14, the mixing mechanism 5050 includes a motor 12, a first rotator 21, a second rotator 5017, a magnetic coupling mechanism, a ring member 5015, a seal ring 14, and a mixing rod 11. The magnetic coupling mechanism magnetically couples the first magnetic disk (first rotator) 21 with the second rotator 5017.

The second rotator 5017 has a configuration similar to that of the second magnetic disk 13 in the above-mentioned embodiment. Hereinafter, similar configurations will be denoted by similar symbols and descriptions thereof may be omitted. The second rotator 5017 is housed in a housing compartment that is each of non-through-holes provided in the housing 201.

The ring member 5015 is a ring for inhibiting a fall, which retains the second rotator 5017 not to fall from the housing compartment. The ring member 5015 is also a slide bearing that supports a rotational shaft of the second rotator 5017.

The ring member 5015 is provided between the second rotator 5017 and the seal ring 14. The ring member 5015 is, for example, retained in the housing 201 by being press-fitted into the housing compartment of the housing 201.

The second rotator 5017 is retained by the ring member 5015 and the housing 201.

An inner diameter of the ring member 5015 is smaller than an outer diameter of a second-magnetic-disk main body 133 of the second rotator 5017 and is larger than an outer diameter of a cylindrical portion 134 of the second rotator 5017. The cylindrical portion 134 of the second rotator 5017 and the ring member 5015 are disposed, forming a clearance therebetween.

The housing 201 and the second rotator 5017 are, for example, formed of at least one of a PEEK resin, a fluorocarbon polymer, and a polyphenylene sulfide.

In the mixing mechanism 5050, the first magnetic disk (first rotator) 21 is connected to the motor 12. Due to activation of the motor 12, the first magnetic disk 21 rotates. The first magnetic disk 21 and the second rotator 5017 are coupled with each other by the magnetic coupling mechanism. The second rotator 5017 rotates, following the first magnetic disk 21. The mixing rod 11 coupled with the second rotator 5017 rotates due to rotation of the second rotator 5017. In this manner, the matter to be mixed in a well 31 is mixed.

A top surface of the second rotator 5017 is held in surface-contact with an inner top surface 201a of the housing compartment of the housing 201 and rotates.

As described above, the mixing mechanism 5050 including the slide bearing may be employed. The housing 201 that houses the second rotator 5017 is capable of closing the well 31 together with the seal ring 14.

Further, in the mixing mechanism 5050, the top surface of the second rotator 5017 is held in surface-contact with the inner top surface 201a of the housing 201 and rotates.

Protrusions may be provided in the center of the top surface of the second rotator 5017 or the inner top surface 201a forming the housing compartment of the housing 201. With these protrusions, the contact area between the top portion of the second rotator 5017 and the inner top surface 201a of the housing 201 decreases and abrasion of the second rotator 5017 and the housing 201 in the contact portion during rotation is thus reduced.

Note that the configuration for reducing abrasion during rotation is not limited to the provision of the protrusions. For example, balls may be provided between the second rotator 5017 and the inner top surface 201a of the housing compartment of the housing 201 for reducing abrasion during rotation. In the case of providing the balls, recesses serving as walls for limiting the movement of the balls may be formed in the top surface of the second rotator 5017 or the inner top surface 201a of the housing 201.

Alternatively, one obtained by integrally molding the seal ring 14 and the ring member 5015 may be used in the mixing mechanism 5050. In this case, the ring member portion is retained in the housing 201 by clearance fit and the seal ring portion is press-fitted into the housing 201 and fixed.

What is claimed is:

1. A mixing device that is configured to install therein a multi-well plate including a plurality of wells capable of containing matter to be mixed and comprises mixing mechanisms each of which mixes the matter to be mixed with a motor and is provided for each of the wells, the mixing mechanisms each including
    a first rotator that is connected to the motor and rotates due to activation of the motor,
    a mixing rod that mixes the matter to be mixed,
    a second rotator that supports the mixing rod,
    a magnetic coupling mechanism that magnetically couples the first rotator to the second rotator, and
    a seal ring that surrounds an opening of the well and is capable of closing the well together with the second rotator.

2. The mixing device according to claim 1, wherein the second rotator includes
    a rotational portion that is coupled to the mixing rod, and
    a bearing provided between the rotational portion and the seal ring.

3. The mixing device according to claim 2, wherein the rotational portion includes a rotational shaft that is coupled to the mixing rod,
    the bearing includes
        an inner race including a through-hole into which the mixing rod and the rotational shaft are inserted,
        an outer race, and
        a ball provided between the inner race and the outer race, and
    the seal ring has an inner diameter equal to or smaller than an outer diameter of the inner race as the seal ring and the inner race are projected onto a plane orthogonal to the rotational shaft.

4. The mixing device according to claim 2, wherein the bearing is formed of at least one of a PEEK resin, a fluorocarbon polymer, and a polyphenylene sulfide.

5. The mixing device according to claim 1, wherein the second rotator includes a rotational portion that is coupled to the mixing rod, the mixing device further comprising
    a ring member provided between the rotational portion and the seal ring.

6. The mixing device according to claim 1, further comprising
    a casing including a main surface portion that is opposed to an upper surface of the multi-well plate, wherein
    the mixing mechanism is provided in the main surface portion.

7. The mixing device according to claim 6, wherein the casing has a stacked structure of
    a motor-housing casing that houses the motor and the first rotator for each of the wells, and
    a housing that retains the mixing rod, the second rotator, and the seal ring for each of the wells.

8. The mixing device according to claim 7, wherein the housing includes
    a first flat surface that is adjacent to the motor-housing casing, and
    a second flat surface that is opposed to the first flat surface, and
    the second flat surface includes housing compartments each having a bottom, being provided for each of the wells, and housing the second rotator.

9. The mixing device according to claim 8, further comprising
    a mounting table on which the multi-well plate is placed.

10. The mixing device according to claim 7, wherein the housing is formed of at least one of a PEEK resin, a fluorocarbon polymer, and a polyphenylene sulfide.

11. The mixing device according to claim 1, wherein the magnetic coupling mechanism includes
    a first magnet provided in the first rotator, and
    a second magnet provided in the second rotator.

12. The mixing device according to claim 11, wherein the first rotator includes a first surface and a second surface that are disposed to be opposed to each other in a rotational-axis direction of the first rotator,
    the first magnet includes two different magnetic poles and is provided in parallel to the rotational-axis direction such that one of the magnetic poles is located on a side of the first surface and the other is located on a side of the second surface, and
    the magnetic poles of the first magnets, which are located on the side of the first surface, are all the same in the mixing mechanisms each provided for each of the wells.

13. The mixing device according to claim 1, wherein the motor is provided for each of the wells.

14. The mixing device according to claim 1, wherein the seal ring is formed of a fluorocarbon polymer or a fluorocarbon rubber.

15. The mixing device according to claim 1, wherein the mixing rod is formed of at least one of a PEEK resin, a fluorocarbon polymer, and a polyphenylene sulfide.

* * * * *